(12) United States Patent
Burwell et al.

(10) Patent No.: US 7,730,894 B2
(45) Date of Patent: Jun. 8, 2010

(54) PHOTODYNAMIC THERAPY APPARATUS AND METHOD FOR VASCULAR TISSUE TREATMENT

(75) Inventors: Phillip Burwell, Snohomish, WA (US); Zihong Guo, Bellevue, WA (US); Jennifer Kristine Matson, Renton, WA (US); Steven Ross Daly, Sammamish, WA (US); David B. Shine, Sammamish, WA (US); Gary Lichttenegger, Woodinville, WA (US); Jean Bishop, Bothell, WA (US); Nick Yeo, Great Bookham (GB); Hugh Narciso, Santa Barbara, CA (US)

(73) Assignee: Light Sciences Oncology, Inc., Bellevue, WA (US)

( * ) Notice: Subject to any disclaimer, the term of this patent is extended or adjusted under 35 U.S.C. 154(b) by 265 days.

(21) Appl. No.: 11/773,555

(22) Filed: Jul. 5, 2007

(65) Prior Publication Data

US 2008/0027517 A1  Jan. 31, 2008

Related U.S. Application Data

(62) Division of application No. 10/799,357, filed on Mar. 12, 2004, now Pat. No. 7,252,677.

(60) Provisional application No. 60/455,069, filed on Mar. 14, 2003.

(51) Int. Cl.
 *A61B 19/00* (2006.01)
(52) U.S. Cl. .............................. 128/898; 606/7; 606/15
(58) Field of Classification Search .................. 606/7, 606/15; 607/88, 89; 128/898
 See application file for complete search history.

(56) References Cited

U.S. PATENT DOCUMENTS

| | | | |
|---|---|---|---|
| 4,423,725 A | 1/1984 | Baran et al. | 128/207.15 |
| 4,445,892 A | 5/1984 | Hussein et al. | 604/101.05 |
| 4,470,407 A | 9/1984 | Hussein | 600/108 |
| 4,763,654 A | 8/1988 | Jang | 606/195 |
| 4,773,899 A | 9/1988 | Spears | 604/20 |
| 4,799,479 A | 1/1989 | Spears | 606/28 |
| 4,820,349 A | 4/1989 | Saab | 606/194 |
| 4,961,738 A * | 10/1990 | Mackin | 606/15 |
| 4,983,167 A | 1/1991 | Sahota | 606/194 |
| 5,019,042 A | 5/1991 | Sahota | 604/101.01 |
| 5,019,075 A | 5/1991 | Spears et al. | 606/7 |
| 5,026,366 A | 6/1991 | Leckrone | 606/7 |
| 5,071,407 A | 12/1991 | Termin et al. | 604/104 |
| 5,090,958 A | 2/1992 | Sahota | 604/98.01 |
| 5,104,392 A | 4/1992 | Kittrell et al. | 606/15 |
| 5,129,889 A | 7/1992 | Hahn et al. | 604/265 |
| 5,147,377 A | 9/1992 | Sahota | 606/194 |
| 5,160,321 A | 11/1992 | Sahota | 604/101.03 |
| 5,169,395 A | 12/1992 | Narciso, Jr. | 606/7 |
| 5,176,619 A | 1/1993 | Segalowitz | 600/18 |
| 5,178,616 A * | 1/1993 | Uemiya et al. | 606/7 |
| 5,217,456 A | 6/1993 | Narciso, Jr. | 606/15 |
| 5,226,430 A | 7/1993 | Spears et al. | 128/898 |
| 5,267,959 A | 12/1993 | Forman | 604/103 |
| 5,290,275 A | 3/1994 | Kittrell et al. | 606/15 |
| 5,330,465 A | 7/1994 | Doiron et al. | 606/7 |
| 5,358,485 A | 10/1994 | Vance et al. | 604/22 |
| 5,370,608 A | 12/1994 | Sahota et al. | 604/20 |
| 5,383,467 A | 1/1995 | Auer et al. | 600/342 |
| 5,406,960 A | 4/1995 | Corso, Jr. | 600/585 |
| 5,415,654 A | 5/1995 | Daikuzono | 606/15 |
| 5,417,653 A | 5/1995 | Sahota et al. | 604/20 |
| 5,441,497 A | 8/1995 | Narciso, Jr. | 606/15 |
| 5,445,608 A * | 8/1995 | Chen et al. | 604/20 |
| 5,454,794 A | 10/1995 | Narciso, Jr. et al. | 607/88 |

(Continued)

FOREIGN PATENT DOCUMENTS

EP  0 755 697  7/1996

(Continued)

OTHER PUBLICATIONS

Nagae, T.; Aizawa, K.; Uchimura, N.' Tani, D.; Abe, M.; Fujishima, K.; Wilson, S.; and Ishimaru, S. "Endovascular Photodynamic Therapy Using Mono-L-Aspartyl-Chlorin e6 to Inhibit Intimal Hyperplasia in Balloon-Injured Rabbit Arteries," *Lasers in Surgery and Medicine*, 28:381-388 (2001). © 2001 Wiley-Liss, Inc.

(Continued)

*Primary Examiner*—Ahmed M Farah
(74) *Attorney, Agent, or Firm*—Ronald M. Anderson

(57) ABSTRACT

Light generating devices for illuminating portions of vascular tissue, to render photodynamic therapy. In one embodiment, a light source array preferably including a plurality of light emitting diodes, a focusing lens, and a light diffusing element are included in a distal end of a catheter. A balloon is optionally provided to interrupt blood flow that can block the transmission of light, and to center the apparatus in a blood vessel. Optical fibers optionally direct light from the light source to the diffusing element. The light source array can have a radial or linear configuration and can produce more than one wavelength of light for activating different photoreactive agents. Linear light source elements are particularly useful to treat elongate portions of tissue in a vessel. One embodiment intended for use with a conventional balloon catheter integrates light sources into a guidewire.

16 Claims, 9 Drawing Sheets

U.S. PATENT DOCUMENTS

| | | | |
|---|---|---|---|
| 5,582,171 A | 12/1996 | Chornenky et al. | 600/425 |
| 5,607,419 A | 3/1997 | Amplatz et al. | 606/7 |
| 5,609,591 A | 3/1997 | Daikuzono | 606/15 |
| 5,662,712 A | 9/1997 | Pathak et al. | 623/23.64 |
| 5,700,243 A | 12/1997 | Narciso, Jr. | 604/102.01 |
| 5,766,234 A | 6/1998 | Chen et al. | 604/92 |
| 5,766,558 A | 6/1998 | Letzsch et al. | 607/92 |
| 5,779,697 A | 7/1998 | Glowa et al. | 606/185 |
| 5,779,731 A | 7/1998 | Leavitt | 606/194 |
| 5,782,896 A | 7/1998 | Chen et al. | 604/88 |
| 5,800,478 A | 9/1998 | Chen et al. | 607/88 |
| 5,830,210 A | 11/1998 | Rudko et al. | 606/15 |
| 5,876,426 A | 3/1999 | Kume et al. | 607/88 |
| 5,947,958 A | 9/1999 | Woodard et al. | 606/15 |
| 5,976,106 A | 11/1999 | Verin et al. | 604/103.07 |
| 5,997,571 A | 12/1999 | Farr et al. | 607/92 |
| 6,013,053 A | 1/2000 | Bower et al. | 604/96.01 |
| 6,024,740 A | 2/2000 | Lesh et al. | 606/34 |
| 6,058,323 A | 5/2000 | Lemelson | 600/408 |
| 6,086,558 A | 7/2000 | Bower et al. | 604/96.01 |
| 6,159,236 A | 12/2000 | Biel | 607/92 |
| 6,171,299 B1 | 1/2001 | Bonutti | 606/1 |
| 6,175,669 B1 | 1/2001 | Colston et al. | 385/12 |
| 6,193,676 B1 | 2/2001 | Winston et al. | 600/585 |
| 6,231,568 B1 | 5/2001 | Loeb et al. | 606/15 |
| 6,245,012 B1 | 6/2001 | Kleshinski | 623/1.11 |
| 6,254,571 B1 | 7/2001 | Hart | 604/107 |
| 6,254,599 B1 | 7/2001 | Lesh et al. | 606/41 |
| 6,290,668 B1 | 9/2001 | Gregory et al. | 604/22 |
| 6,299,599 B1 | 10/2001 | Pham et al. | 604/113 |
| 6,336,934 B1 | 1/2002 | Gilson et al. | 606/200 |
| 6,355,030 B1 | 3/2002 | Aldrich et al. | 606/28 |
| 6,416,511 B1 | 7/2002 | Lesh et al. | 606/41 |
| 6,468,244 B1 | 10/2002 | Leone et al. | 604/103.02 |
| 6,485,502 B2 | 11/2002 | Don Michael et al. | 606/200 |
| 6,496,737 B2 | 12/2002 | Rudie et al. | 607/101 |
| 6,508,784 B1 | 1/2003 | Shu | 604/96.01 |
| 6,540,767 B1 | 4/2003 | Walak et al. | 606/200 |
| 6,562,031 B2 | 5/2003 | Chandrasekaran et al. | 606/41 |
| 6,562,058 B2 | 5/2003 | Seguin et al. | 606/200 |
| 6,575,965 B1 | 6/2003 | Benett et al. | 606/15 |
| 6,575,966 B2 * | 6/2003 | Lane et al. | 606/21 |
| 6,585,655 B2 | 7/2003 | Crowley | 600/463 |
| 6,605,030 B2 | 8/2003 | Weinberger | 600/3 |
| 6,616,629 B1 | 9/2003 | Verin et al. | 604/101.05 |
| 6,634,765 B2 | 10/2003 | Lin | 362/249 |
| 6,656,174 B1 | 12/2003 | Hegde et al. | 606/41 |
| 6,749,623 B1 | 6/2004 | Hsi et al. | 607/88 |
| 6,811,562 B1 | 11/2004 | Pless | 607/88 |
| 6,830,584 B1 | 12/2004 | Seguin | 623/2.11 |
| 6,872,205 B2 | 3/2005 | Lesh et al. | 606/41 |
| 6,953,457 B2 | 10/2005 | Farr et al. | 606/15 |
| 6,962,584 B1 | 11/2005 | Stone et al. | 606/7 |
| 7,396,354 B2 * | 7/2008 | Rychnovsky et al. | 606/15 |
| 2001/0029337 A1 | 10/2001 | Pantages et al. | 600/463 |
| 2003/0114744 A1 | 6/2003 | Pantages et al. | 600/407 |
| 2003/0195495 A1 | 10/2003 | Ryan et al. | 606/15 |
| 2005/0038419 A9 | 2/2005 | Arnold et al. | 606/15 |
| 2005/0197534 A1 | 9/2005 | Barbato et al. | 600/173 |
| 2005/0251131 A1 | 11/2005 | Lesh | 606/41 |
| 2007/0010782 A1 | 1/2007 | Doty et al. | 604/20 |
| 2007/0038204 A1 | 2/2007 | Chen et al. | 606/17 |

FOREIGN PATENT DOCUMENTS

| | | |
|---|---|---|
| EP | 0 820 786 | 1/1998 |
| JP | 02-185269 | 7/1990 |
| JP | 07-095986 | 4/1995 |
| JP | 2001-129094 | 5/2001 |
| WO | WO 96/00527 | 1/1996 |
| WO | WO 96/29943 | 10/1996 |
| WO | WO 97/32520 | 9/1997 |
| WO | WO 98/32493 | 7/1998 |
| WO | WO 02/07629 | 1/2002 |
| WO | WO 04/82736 | 9/2004 |

OTHER PUBLICATIONS

Nordenström, Björn. "Balloon Catheters for Percutaneous Insertion Into the Vascular System," Department of Diagnostic Roentgenology, Thoraxkliniken, Karolinska Sjukhuset, Stockholm, Sweden. pp. 411-416. Mar. 2, 1962.

Nordenström, Björn. "New Instruments for Catheterization and Angiocardiography," Department of Roentgenology, Thoraxkliniken, Karolinska Sjukhuset, Stockholm, Sweden. Aug. 1965, pp. 256-259.

* cited by examiner

PHOTODYNAMIC THERAPY APPARATUS AND METHOD FOR VASCULAR TISSUE TREATMENT

RELATED APPLICATIONS

This application is a divisional of a copending patent application Ser. No. 10/799,357, filed on Mar. 12, 2004, which itself is based on a prior copending provisional application Ser. No. 60/455,069, filed on Mar. 14, 2003, the benefit of the filing dates of which are hereby claimed under 35 U.S.C. §119(e) and 120.

BACKGROUND

Photodynamic therapy (PDT) is a process whereby light of a specific wavelength or waveband is directed to tissues undergoing treatment or investigation, which have been rendered photosensitive through the administration of a photoreactive or photosensitizing agent. Thus, in this therapy, a photoreactive agent having a characteristic light absorption waveband is first administered to a patient, typically by intravenous injection, oral administration, or by local delivery to the treatment site. Abnormal tissue in the body is known to selectively absorb certain photoreactive agents to a much greater extent than normal tissue. Once the abnormal tissue has absorbed or linked with the photoreactive agent, the abnormal tissue can then be treated by administering light of an appropriate wavelength or waveband corresponding to the absorption wavelength or waveband of the photoreactive agent. Such treatment can result in the necrosis of the abnormal tissue.

PDT has proven to be very effective in destroying abnormal tissue such as cancer cells and has also been proposed for the treatment of vascular diseases, such as atherosclerosis and restenosis due to intimal hyperplasia. In the past percutaneous transluminal coronary angioplasty (PTCA) has typically been performed to treat atherosclerotic cardiovascular diseases. A more recent treatment based on the use of drug eluting stents has reduced the rate of restenosis in some diseased vessels. As effective as such therapies are, a new platform of therapy is needed for treating peripheral arterial disease and more problematic coronary diseases, such as vulnerable plaque, saphenous vein bypass graft disease, and diffuse long lesions.

The objective of PDT may be either diagnostic or therapeutic. In diagnostic applications, the wavelength of light is selected to cause the photoreactive agent to fluoresce, thus yielding information about the tissue without damaging the tissue. In therapeutic applications, the wavelength of light delivered to the tissue treated with the photoreactive agent causes the photoreactive agent to undergo a photochemical reaction with oxygen in the localized tissue, to yield free radical species (such as singlet oxygen), which cause localized cell lysis or necrosis. The central strategy to inhibit arterial restenosis using PDT, for example, is to cause a depletion of vascular smooth muscle cells, which are a source of neointima cell proliferation (see, Nagae et al., *Lasers in Surgery and Medicine* 28:381-388, 2001). One of the advantages of PDT is that it is a targeted technique, in that selective or preferential delivery of the photoreactive agent to specific tissue enables only the selected tissue to be treated. Preferential localization of a photoreactive agent in areas of arterial injury, with little or no photoreactive agent delivered to healthy portions of the arterial wall, can therefore enable highly specific PDT ablation of arterial tissue.

Light delivery systems for PDT are well known in the art. Delivery of light from a light source, such as a laser, to the treatment site has been accomplished through the use of a single optical fiber delivery system with special light-diffusing tips affixed thereto. Exemplary prior art devices also include single optical fiber cylindrical diffusers, spherical diffusers, micro-lensing systems, an over-the-wire cylindrical diffusing multi-optical fiber catheter, and a light-diffusing optical fiber guidewire. Such prior art PDT illumination systems generally employ remotely disposed high power lasers or solid state laser diode arrays, coupled to optical fibers for delivery of light to a treatment sight. The disadvantages of using laser light sources include relatively high capital costs, relatively large size, complex operating procedures, and the safety issues inherent when working with high power lasers. Accordingly, there is a tremendous need for a light generating system that requires no lasers, and which generates light at the treatment site. For vascular application of PDT, it would be desirable to provide a light-generating apparatus having a minimal cross-section, a high degree of flexibility, and compatibility with a guidewire, so the light-generating apparatus can be delivered to the treatment site. Such an apparatus should provide a light uniformly to the treatment area.

For vascular application of PDT, it would be further desirable to provide a light-generating apparatus configured to be centered within a blood vessel, and which is configured to remove light absorbent material, such as blood, from the light path between the target tissue and the apparatus. Typically, centering of apparatus within a vessel can be achieved with an inflatable balloon catheter that matches the diameter of the blood vessel when the balloon is inflated. Such devices desirably occlude blood flow, enabling the light path to remain clear of obstructing blood. However, a single balloon is not sufficient to treat lesions in coronary blood vessels that are greater than about 30 mm in length, because a single inflated balloon may not provide good centering of the apparatus within such a long section. Therefore, it would be desirable to provide a light-generating apparatus that is configured treat long lesions or long vessel segments.

SUMMARY

The present invention encompasses light generating devices for illuminating portions of vascular tissue to enable PDT to be provided. Each embodiment includes one or more light sources configured to be positioned inside a body cavity or a vascular system. While the term "light source array" is frequently employed herein, because particularly preferred embodiments of this invention include multiple light sources arranged in a radial or linear configuration, it should be understood that a single light source could be employed. Using a plurality of light sources enables larger treatment areas to be illuminated. Light emitting diodes (LEDs) are particularly preferred as light sources, although other types of light sources can be employed, as will be described in detail below. The light source that is used will be selected based on the characteristics of a photoreactive agent in connection with which the apparatus is intended to be used, since light of incorrect wavelengths will not cause the desired reaction by the photoreactive agent. Light source arrays can include light sources that provide more than one wavelength or waveband of light. Linear light source arrays are particularly useful to treat elongate portions of tissue. Light source arrays can also include reflective elements to enhance the transmission of light in a preferred direction. Each embodiment described herein can beneficially include expandable members such as inflatable balloons to occlude blood flow (which can interfere with the transmission of light from the light source to the intended target tissue) and to enable the apparatus to be centered in a blood vessel.

In configurations where light is intended to be directed through such expandable members to reach target tissue, the expandable members are preferably constructed from materials that substantially transmit the required wavelength of light. Bio-compatible polymers having the required optical characteristics are particularly preferred. Where light is directed through such expandable members to reach target tissue, a fluid used to inflate the expandable members can include additives to enhance the transmission or diffusion of light. In configurations where an expandable member is disposed proximate to a light source array, the fluid used to expand the member acts as a heat sink to absorb heat generated by the light source array. Regularly replacing the fluid within the expandable member will enhance the cooling effects. Positioning aids, such as radio-opaque markers, can be included to enable any of the embodiments described in detail below to be properly positioned with respect to a target area.

A first preferred embodiment is configured to emit light from a distal tip of an elongate flexible body. The first preferred embodiment includes an elongate flexible body having a distal end and a proximal end, with at least one lumen extending therebetween. A distal portion of the first embodiment includes a light source array and a light diffusing element configured to disperse light from the light source array outward from the distal tip of the apparatus. An electrical lead extends from the light source array to at least a proximal end of the elongate flexible body, so that the electrical lead can be coupled to an external power source to energize the light source array. A focusing lens and one or more optical fibers are preferably disposed between the light source array and the light diffusing element. Incorporating a lumen extending through the apparatus enables the apparatus to be advanced to a desired position using a guidewire. A radio-opaque material can be included immediately adjacent to the light diffusing element to facilitate the proper positioning of the light diffusing element relative to a target area. A radially oriented light source array is used in such a first preferred embodiment.

A second preferred embodiment is similar to the first preferred embodiment, but further includes a tapered optical fiber, or bundle of optical fibers, disposed between the light source array and the light diffusing element, such that the light diffusing element has a smaller cross sectional area than does the light source array. An inflatable balloon encompasses substantially the entire light diffusing element, and in this embodiment, the elongate flexible body, the light source array, and the tapered optical fiber include an inflation lumen in fluid communication with the inflatable balloon. The light source array preferably includes reflective elements disposed to maximize the intensity of light directed toward the light diffusing element.

Another preferred embodiment includes an elongate flexible body with a linear light source array coupled to a distal end of the elongate flexible body. The linear light source array must be sufficiently flexible to enable the apparatus to be advanced through a vascular system, and preferably includes a plurality of LEDs attached to a flexible conductive substrate. Encapsulating the light source array in a flexible cover, such as a polymer, will protect the light source array from damage. Of course, such a cover must be substantially optically transparent to the required wavelengths of light. Additives can be added to the material of the cover to enhance the transmission or diffusion of light emitted from the light source array. A distal portion is coupled to a distal end of the light source array. The distal portion includes an opening on a sidewall of the distal portion, and an opening on the distal end of the distal portion, with a lumen extending therebetween to enable the apparatus to be advanced over a guidewire. The linear light source array is not configured to include a lumen for a guide wire, so the opening in the sidewall of the distal portion is required to enable the apparatus to be used with a guidewire. It should be understood that a lumen for a guidewire can also be included in the polymer cover that encapsulates the light source array, if it is desired to include a guidewire lumen through each section of the apparatus.

Preferably, this embodiment includes an expandable member disposed to substantially encompass the light source array. Accordingly, the elongate flexible body includes an inflation lumen to enable the expandable member to be inflated. Preferably, each end of the light source array is marked with a radio-opaque tag (or some other type of identifier) so that the light source array can be properly positioned adjacent to target tissue. The length of the linear array is only limited by the length of the expandable member. If the linear array is made longer than the expandable member, light emitted from that portion of the linear array extending beyond the expandable member will be blocked by blood, and is not likely to reach the target tissue. As described below, the use of a plurality of expandable members enables longer linear light sources to be used.

Use of a linear light source array in an apparatus configured in accord with the present invention requires that the array be sufficiently flexible to enable the resulting device to be advanced through a vascular system. LEDs are sufficiently small and compact, so that when LEDs are mounted to a flexible conductive substrate, a flexible light source array is achieved that meets this requirement. The flexibility of the linear light source array can be further enhanced by including strain relief elements in the light source array. Also, including a plurality of folds or bends in the flexible conductive substrate will further enhance the flexibility of the substrate. The polymer employed to encapsulate the LEDs and conductive substrate is preferably selected to be both optically transparent to the required wavelength of the light used, and sufficiently flexible.

Yet another aspect of the present invention is directed to the incorporation of light emitting devices, preferably LEDs, in a guidewire. Such a guidewire is used with a catheter, preferably one including one or more expandable members. A conventional guidewire is modified to include a conductive core enabling light sources to be coupled to an external power supply, and a plurality of orifices are formed into the guidewire. The orifices extend to the conductive core, so that light sources can be inserted into the orifices and electrically coupled to the conductive core. Each light source is then electrically coupled through the conductive core to an external lead that enables a complete circuit to be achieved to energize the light sources. The guidewire, external lead, and light sources are then covered with a flexible polymer which should be substantially optically transparent to the required wavelength or waveband of light, at least where the flexible polymer overlies the light sources.

Still another aspect of the present invention employs at least two expandable members to enable a longer portion of a blood vessel to be isolated from blood that would interfere with the transmission of light, compared to the length that can be achieved with a single expandable member. This embodiment is based on an elongate flexible body including at least two expandable members, at least two inflation lumens enabling the expandable members to be inflated, and a lumen for a flushing fluid. A relatively long light source array (i.e., a light source array having a length greater than a length of any one of the expandable members) is disposed between a most proximally positioned expandable member and a most distally positioned proximal member. Preferably, radio-opaque markers are disposed adjacent to the most proximally positioned expandable member and the most distally positioned proximal member. The elongate flexible body includes at least one port coupled in fluid communication to the flushing lumen and disposed between the most proximally positioned expandable member and the most distally positioned proximal member.

In embodiments including two inflation lumens, the apparatus is configured such that the most proximal expandable member is in fluid communication with the first inflation lumen, while other expandable members (those distal to the most proximal expandable member) are coupled in fluid communication with the other inflation lumen. Once the elongate flexible body is positioned within a blood vessel such that a target area is disposed between the most proximally positioned expandable member and the most distally positioned proximal member, the most proximal expandable member is expanded. Then, the flushing fluid is then introduced into the portion of the blood vessel distal to the activated expandable member. After sufficient flushing fluid has displaced the blood flow, the more distal expandable member(s) are inflated using the other inflation lumen, thereby isolating the portion of the blood vessel between the inflated expandable members (that portion being now filled with flushing fluid rather than blood).

In embodiments including an inflation lumen for each expandable member, each expandable member is inflated sequentially, and flushing fluid is also sequentially introduced into the blood vessel. These embodiments require flushing fluid ports to be disposed between each expandable member.

It should be noted that inflating a most proximally positioned expandable member first is appropriate when blood flow in the blood vessel naturally moves from a proximal portion of the apparatus toward a more distal portion. If the blood flow is in the opposite direction, it would be appropriate to configure the apparatus to enable the most distally positioned expandable member to be inflated first. If each expandable member has a dedicated inflation lumen, the order by which the various expandable members are activated can be varied as desired.

In regard to the linear light source array used to illuminate the target area isolated by the two or more expandable members, in one particularly preferred embodiment, the linear light source array is incorporated in the elongate flexible body. Electrical leads used to energize the light source array extend through the elongate flexible member and are adapted to couple to an external power supply. A distal portion is attached to a distal end of the linear light source array, and an orifice is included in the sidewall of the distal portion, and in the distal end of the distal portion (with a lumen extending therebetween). These two orifices enable the apparatus to be positioned using a guidewire. Alternatively, the elongate flexible body and the linear light source array can include a guidewire lumen.

In another particularly preferred embodiment, the linear light source array is not part of or attached to the elongate flexible body. Instead, the linear light source array is integrated into a guide wire, producing an illuminated guidewire that includes markings enabling the light sources on the guidewire to be properly positioned with respect to the portion of the blood vessel isolated by the expandable members.

The embodiments described above are used with a photoreactive agent that is introduced into the target area prior to the apparatus being introduced into the blood vessel. However, it will be understood that if desired, the apparatus can optionally include a lumen for delivering a photoreactive agent into the target area. The resulting embodiments are likely to be particularly beneficial where uptake of the photoreactive agent into the target tissues is relatively rapid, so that the apparatus does not need to remain in the blood vessel for an extended period of time while the photoreactive agent is distributed into and absorbed by the target tissue.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 schematically illustrates a first embodiment of a light-generating apparatus suitable for intra vascular use in accord with the present invention;

Figure 2:
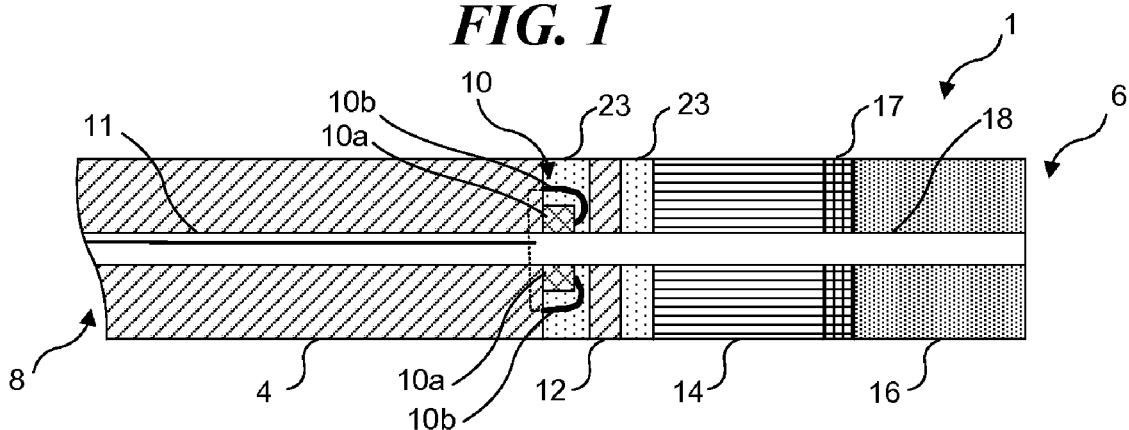
FIG. 2 is a longitudinal cross-sectional view of the light-generating apparatus of FIG. 1.
Figure 4A:
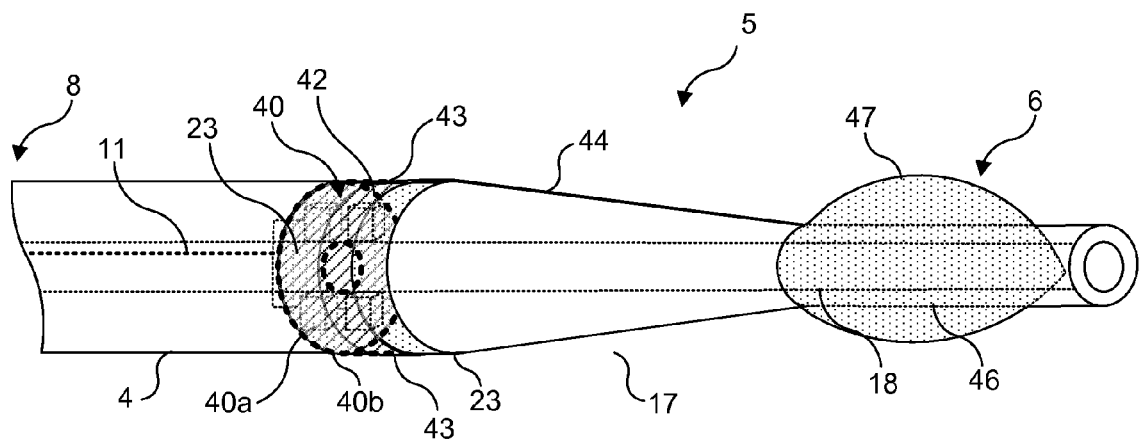
Figure 4B:
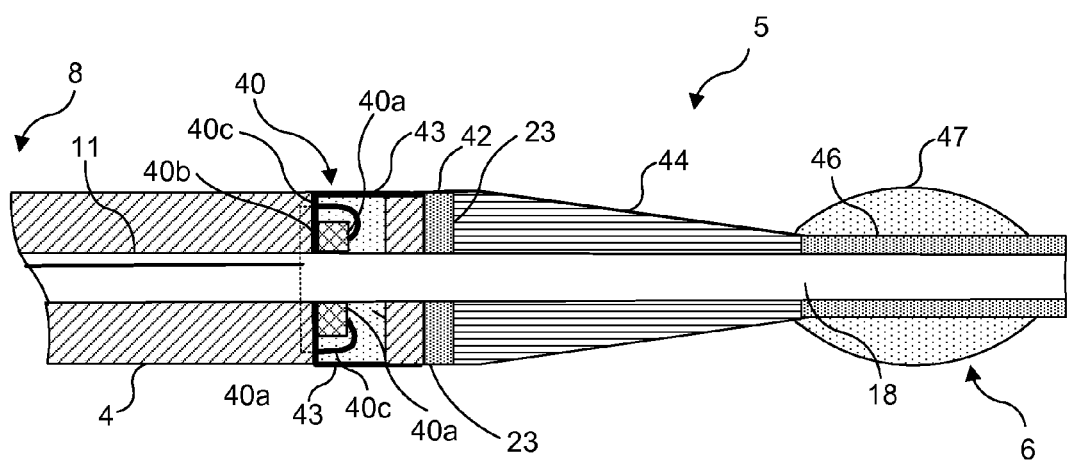
Figure 5:
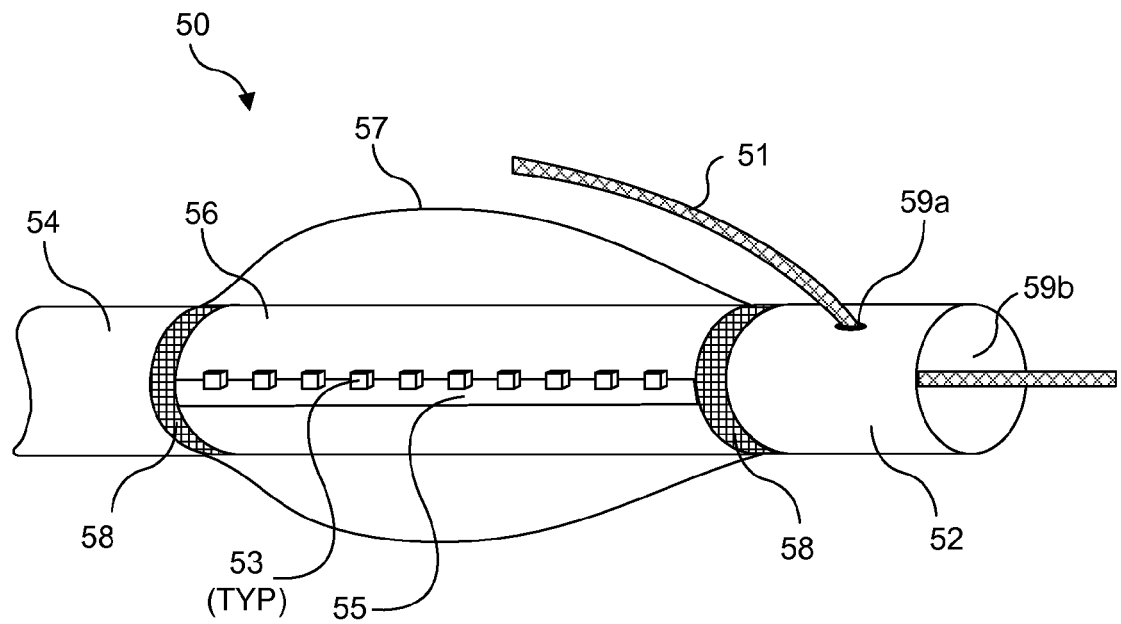
Figure 15:
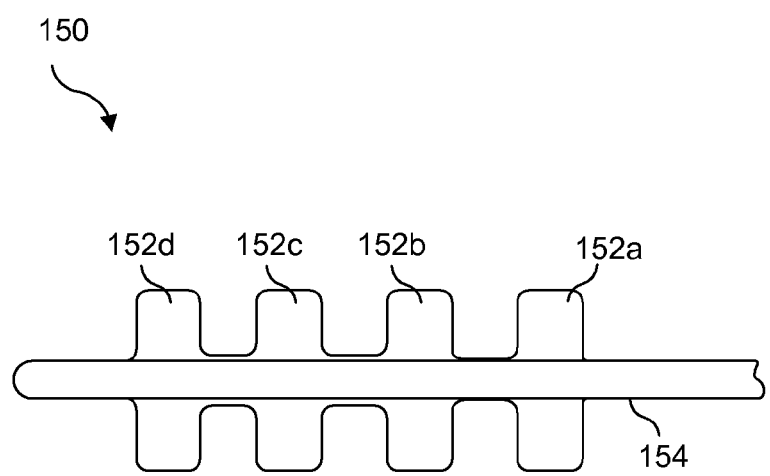
Figure 6:
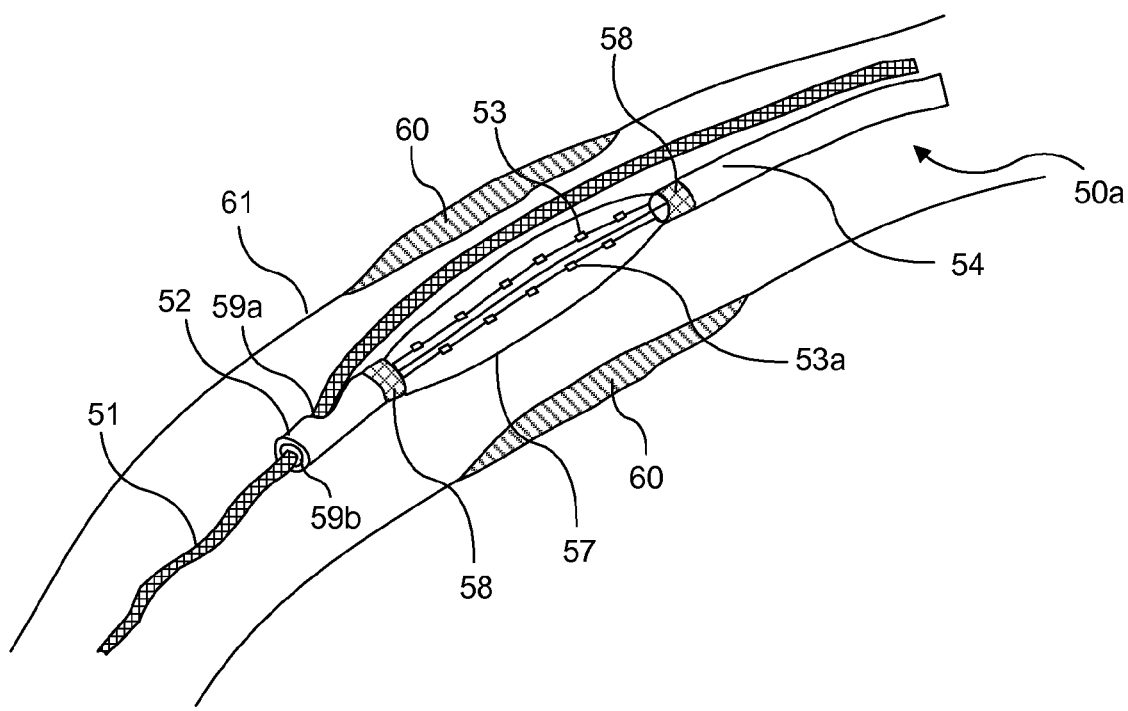
Figure 7:
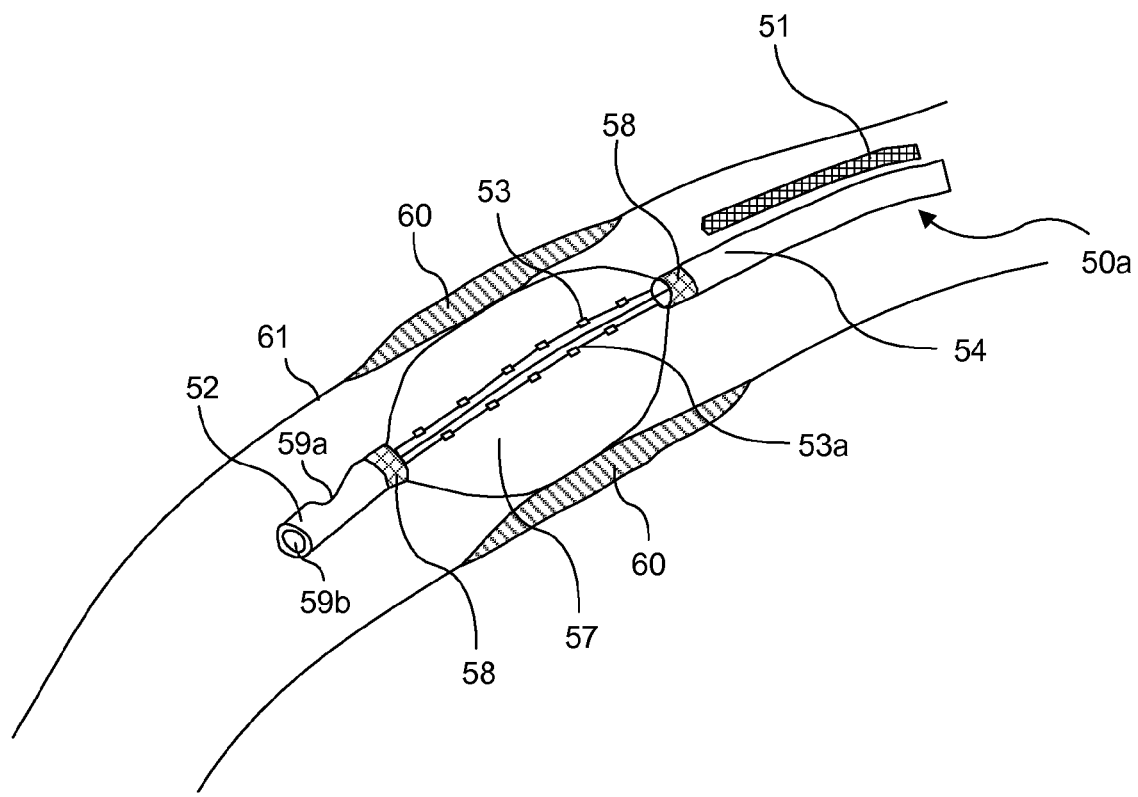
Figure 8:
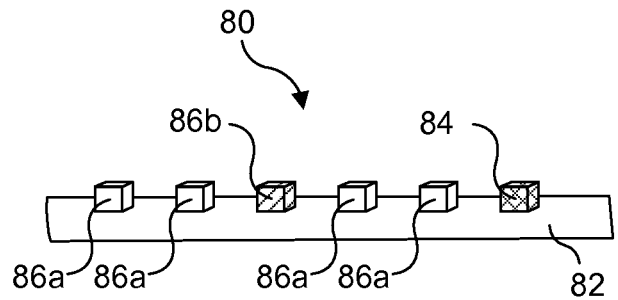
Figure 9A:
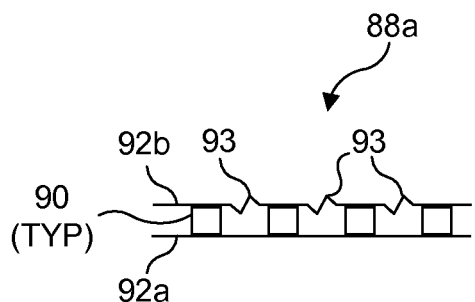
Figure 9B:
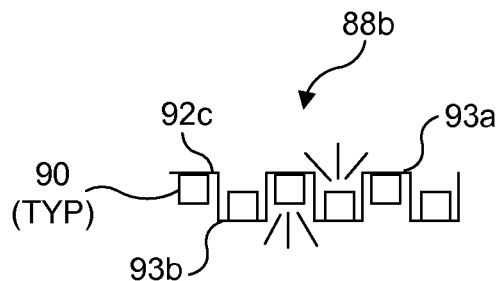
Figure 9C:
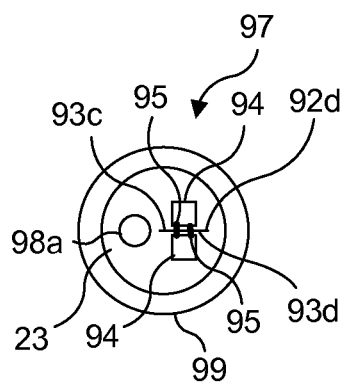
Figure 9D:
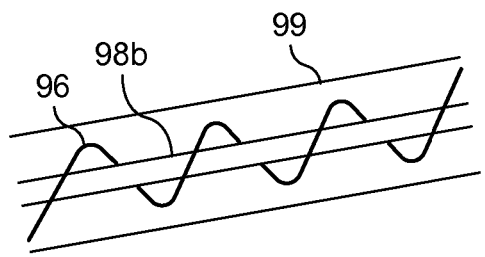
Figure 10:
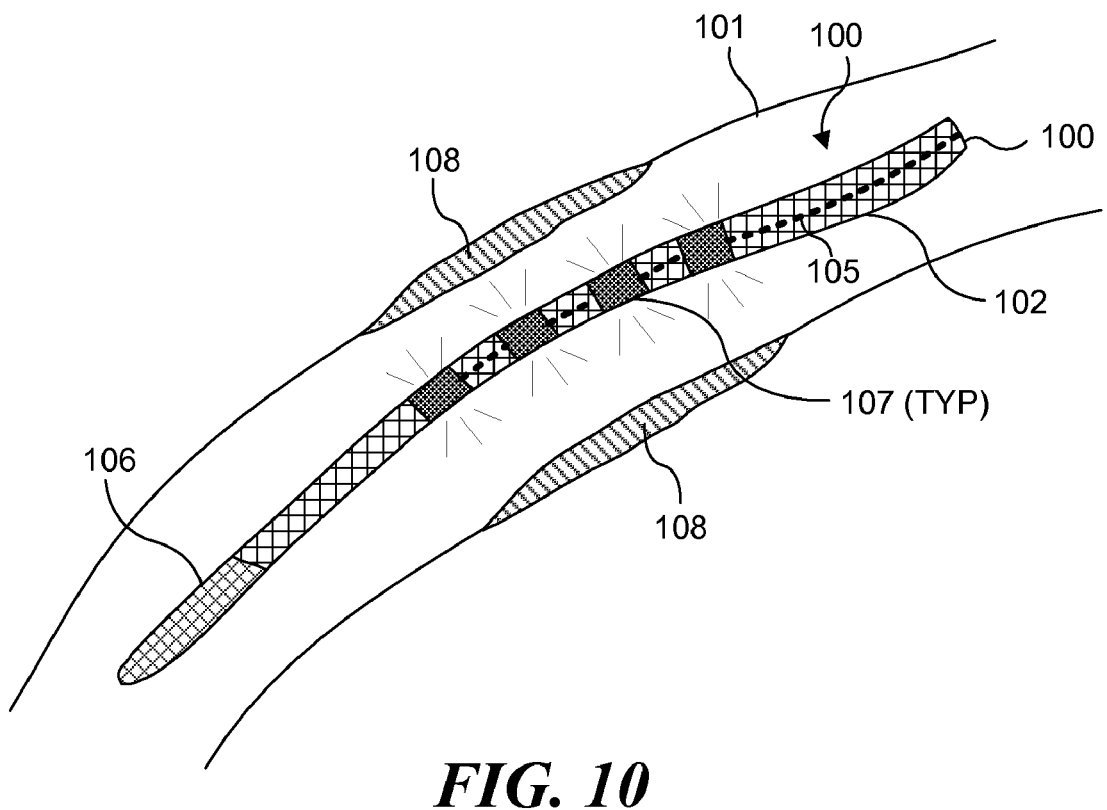
Figure 11:
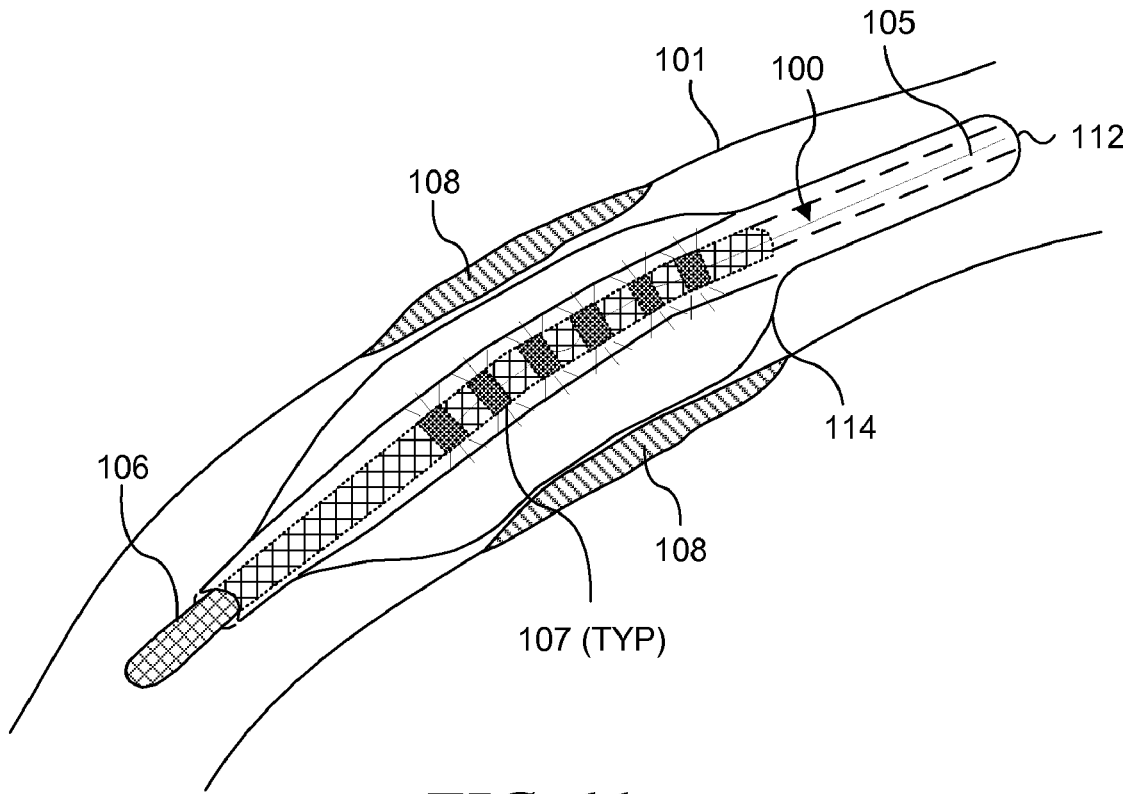
Figure 12A:
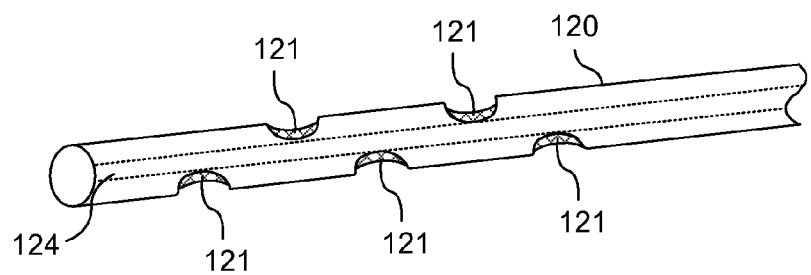
Figure 12B:
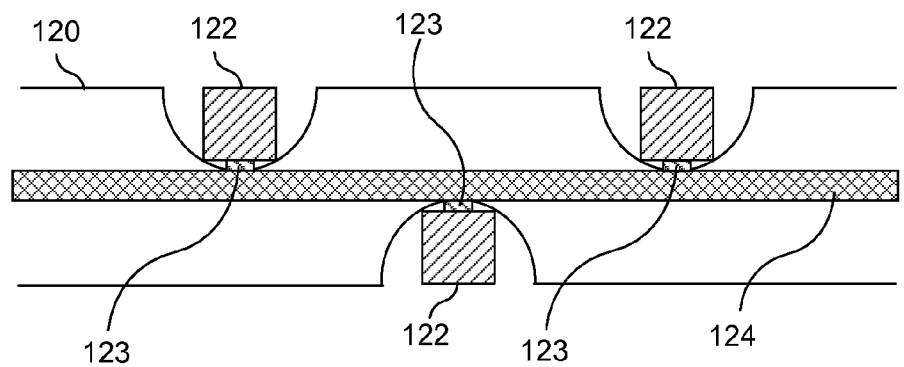
Figure 12C:
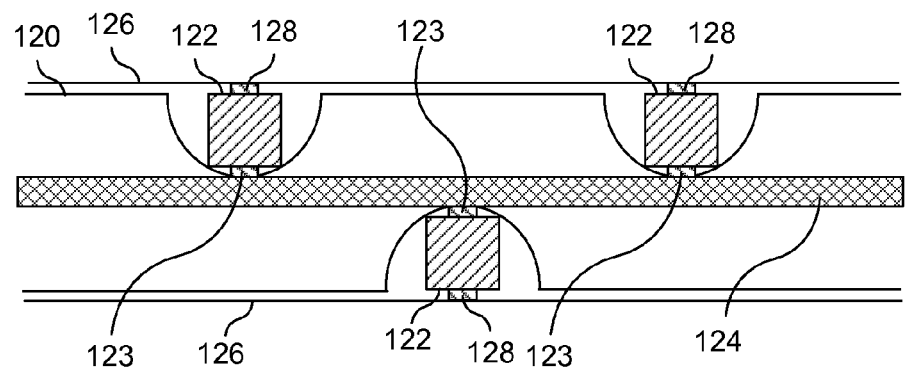
Figure 12D:
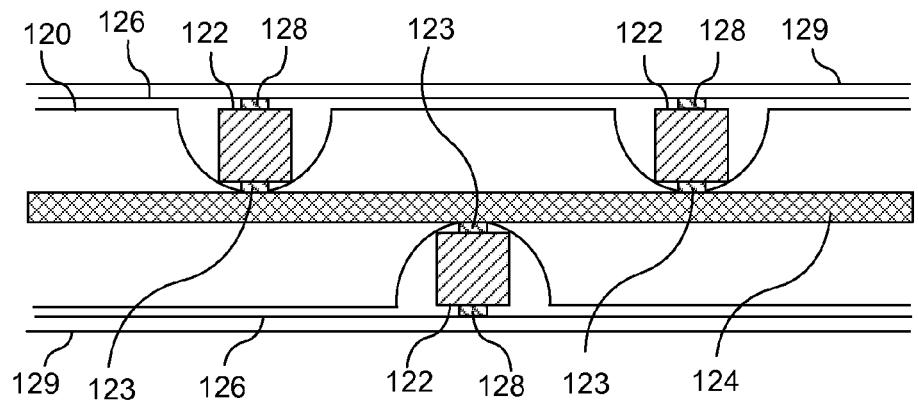
Figure 13A:
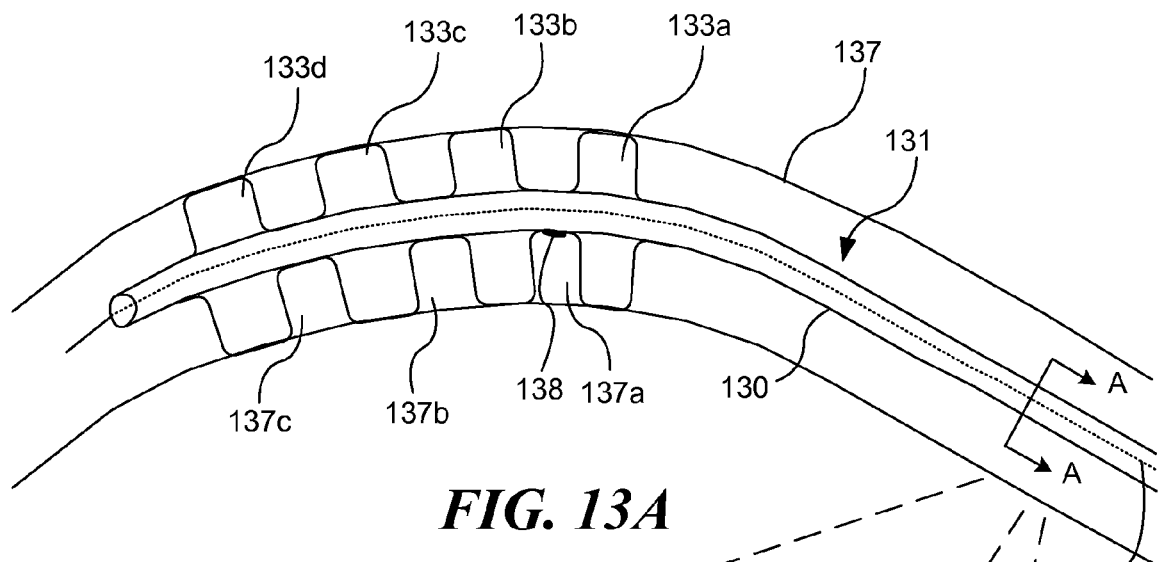
Figure 13B:
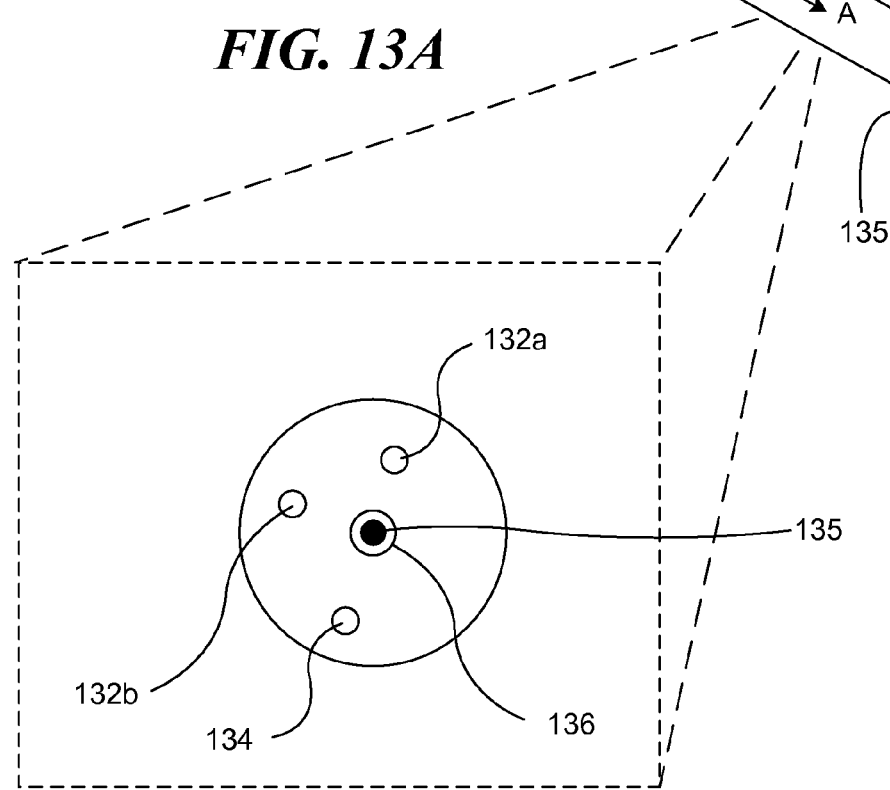
Figure 14A:
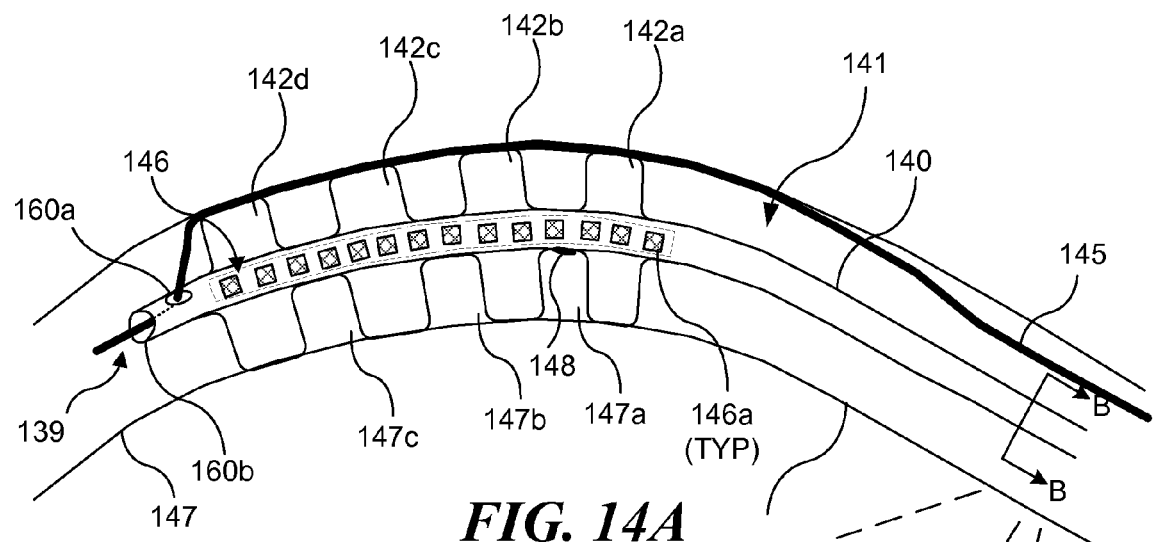
Figure 14B:
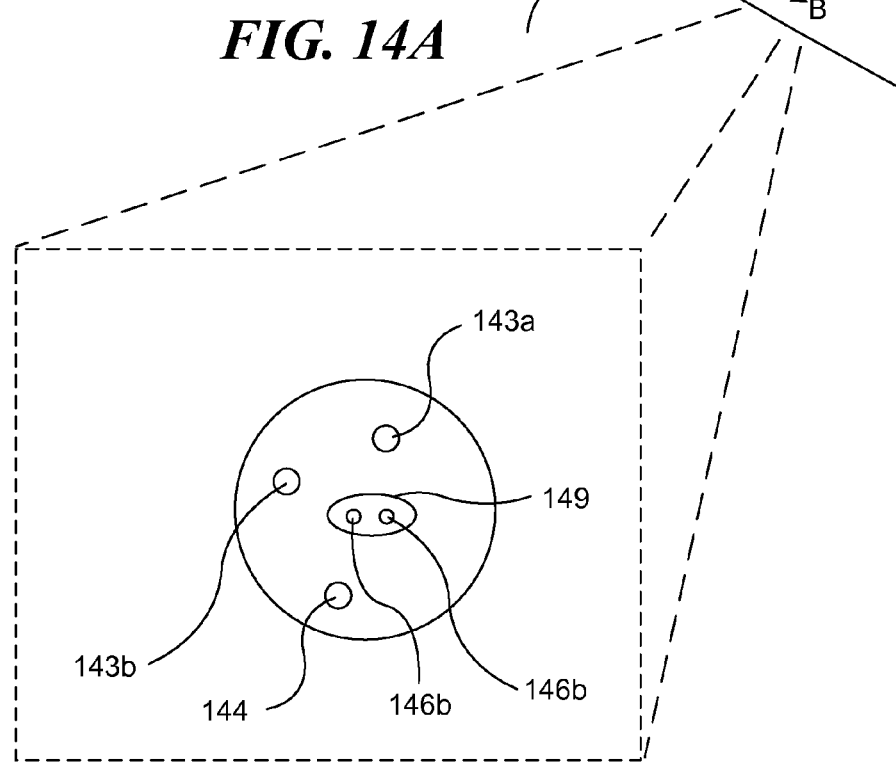

FIG. 4A schematically illustrates a second embodiment of a light-generating apparatus suitable for intra vascular use in accord with the present invention;

FIG. 4B is a longitudinal cross-section view of the light-generating apparatus of FIG. 2;

FIG. 5 schematically illustrates yet another embodiment of a light-generating apparatus suitable for intra vascular use in accord with the present invention;

FIG. 6 schematically illustrates the light-generating apparatus of FIG. 5 being positioned within a blood vessel;

FIG. 7 schematically illustrates the light-generating apparatus of FIGS. 5 and 6 being activated within a blood vessel;

FIG. 8 schematically illustrates a multicolor light array for use in the light-generating apparatus of FIG. 5;

FIGS. 9A and 9B schematically illustrate configurations of light arrays including strain relief features for enhanced flexibility for use in a light-generating apparatus in accord with the present invention;

FIG. 9C is cross-sectional view of a light-generating apparatus in accord with the present invention, showing one preferred configuration of how the light emitting array is positioned relative to the guidewire used to position the light-generating apparatus;

FIG. 9D schematically illustrates a portion of a light-generating apparatus in accord with the present invention, showing how in another preferred configuration, the light emitting array is positioned relative to the guidewire used to position the light-generating apparatus;

FIG. 10 schematically illustrates an embodiment of a light-generating apparatus in which light emitting elements are incorporated into a guidewire, as the apparatus is being positioned within a blood vessel;

FIG. 11 schematically illustrates another embodiment of a light-generating apparatus, in which light emitting elements are incorporated into a guidewire and which includes an inflatable balloon, showing the apparatus being positioned within a blood vessel;

FIG. 12A schematically illustrates a modified guidewire for use in the light-generating apparatus of FIGS. 10 and 11;

FIGS. 12B-12D are cross-sectional views of the guidewire of FIG. 12A, showing details of how the light emitting elements are integrated into the guidewire;

FIG. 13A schematically illustrates still another embodiment of a light-generating apparatus, which includes a plurality of inflatable balloons, as the apparatus is being positioned within a blood vessel;

FIG. 13B is a cross-sectional view of the light-generating apparatus of FIG. 13A;

FIG. 14A schematically illustrates an alternative configuration of a light-generating apparatus including a plurality of inflatable balloons, as the apparatus is being positioned within a blood vessel;

FIG. 14B is a cross-sectional view of the light-generating apparatus of FIG. 14A; and FIG. 15 schematically illustrates a plurality of balloons included with a light-generating apparatus in accord with the present invention.

DESCRIPTION

Figures and Disclosed Embodiments are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Unless otherwise defined, it should be understood that each technical and scientific term used herein and in the claims that follow is intended to be interpreted in a manner consistent with the meaning of that term as it would be understood by one of skill in the art to which this invention belongs. The drawings and disclosure of all patents and publications referred to herein are hereby specifically incorporated herein by reference. In the event that more than one definition is provided herein, the explicitly defined definition controls.

Figure 1:
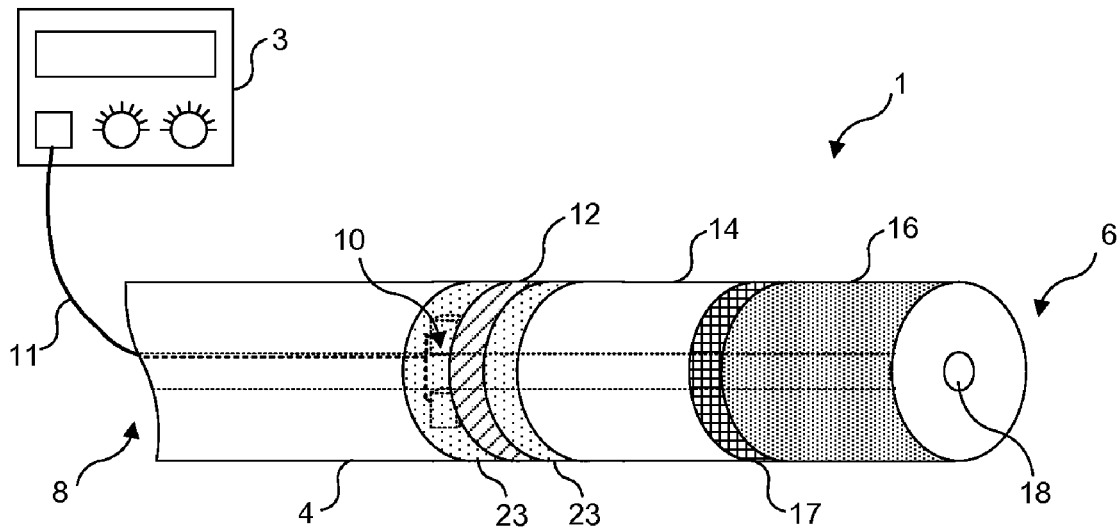

Referring to FIG. 1, a light-generating apparatus 1, having a distal end 6 and a proximal end 8, is embodied in a catheter having an elongate, flexible body 4 formed from a suitable biocompatible material, such as a polymer or metal. Catheter body 4 includes at least one lumen 18. While lumen 18 is shown as centrally disposed within catheter body 4, it should be understood that lumen 18 can be disposed in other positions, and that other lumens, such as lumens for inflating a balloon or delivering a fluid (neither separately shown) can also be included and disposed at locations other than along a central axis of catheter body 4. Lumen 18 has a diameter sufficient to accommodate a guidewire and extends between distal end 6 and proximal end 8 of the catheter, passing through each portion of light-generating apparatus 1. FIG. 1 is not drawn to scale, and a majority of light-generating apparatus 1 shown in FIG. 1 relates to elements disposed near distal end 6. It should be understood that light-generating apparatus 1 is preferably of sufficient length to be positioned so that distal end 6 is disposed at a treatment site within a patient's body, while proximal end 8 is disposed outside of the patient's body, so that a physician or surgeon can manipulate light-generating apparatus 1 with the proximal end.

A light source array 10 includes a plurality of light emitting devices, which are preferably LEDs disposed on conductive traces electrically connected to lead 11. Lead 1 extends proximally through lumen 18 and is coupled to an external power supply and control device 3. While lead 11 is shown as a single line, it should be understood that lead 11 includes at least two separate conductors, enabling a complete circuit to be formed that supplies current to the light emitting devices from the external power supply. As an alternative to LEDs, other sources of light may instead be used, including but not limited to, organic LEDs, super luminescent diodes, laser diodes, and light emitting polymers. In a preferred embodiment, each LED of light source array 10 is encapsulated in a polymer layer 23. Preferably, collection optics 12 are similarly encapsulated in polymer layer 23. Light source array 10 is preferably coupled to collection optics 12, although it should be understood that collection optics 12, while preferred, are not required. When present, collection optics 12 are coupled to either a single optical fiber 14, or an optical fiber bundle (not separately shown). Distal to optical fiber 14 is a light-diffusing tip 16, which can be implemented using glass or plastic. Light emitted from light source array 10 passes through collection optics 12, which focus the light toward optical fiber 14. Light conducted along optical fiber 14 enters diffusing tip 16 at distal end 6 and is scattered uniformly. Preferably, diffusing tip 16 includes a radio-opaque marker 17 to facilitate fluoroscopic placement of distal end 6.

FIG. 2 illustrates a longitudinal cross-section view of light-generating apparatus 1. Collection optics 12 (e.g., a lens) are bonded to light source array 10 and optical fiber 14 by polymer layers 23, and the polymer layer is preferably an epoxy that is optically transparent to the wavelengths of light required to activate the photoreactive agent that is being used. Individual LEDs 10a and leads 10b (each coupling to lead 11) can be clearly seen.

Figure 3A:
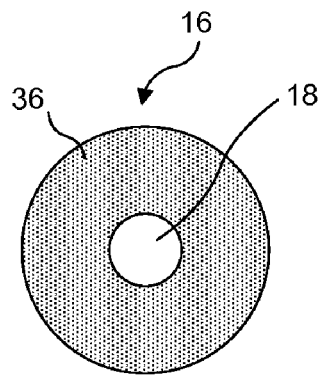
FIGS. 3A and 3B are exemplary radial cross-sectional views of two different embodiments of the light-diffusing portion of the light-generating apparatus of FIG. 1.
Figure 3B:
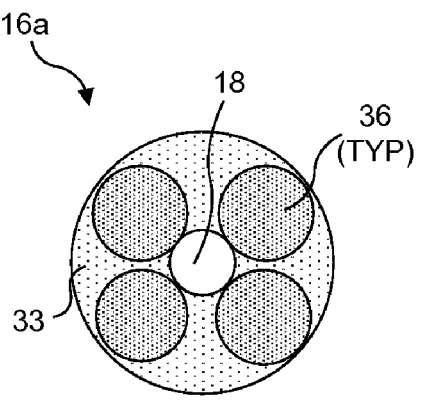

FIG. 3A is a radial cross-sectional view of diffusing tip 16, which includes one diffusing portion 36 and lumen 18. FIG. 3B is a radial cross-sectional view of an alternative diffusing tip 16a, which includes a plurality of diffusing portions 36 encapsulated in a polymer 33, and lumen 18. Polymer 33 preferably comprises an epoxy, and while such an epoxy will likely be optically transparent to the wavelengths of light required to activate the photoreactive agent being utilized; however, because the light will be transmitted by diffusion portions 36, polymer 33 is not required to be optically transparent to these wavelengths. In some applications, it may be desirable to prevent light of any wavelength that can activate the photoreactive agent from exiting a light-generating apparatus other than from its distal end, and polymers do not transmit such wavelengths can be used to block such light.

Turning now to FIG. 4A, another embodiment of a light generating catheter is schematically illustrated. A light-generating apparatus 5 is similarly based a catheter having body 4, including lumen 18, and includes distal end 6 and proximal end 8. As discussed above, while only a single lumen configured to accommodate a guidewire is shown, it should be understood that light-generating apparatus 5 can be configured to include additional lumens as well (such as those used for balloon inflation/deflation). Note that FIGS. 4A and 4B are not drawn to scale; with distal end 6 being is emphasized over proximal end 8.

Light-generating apparatus 5 includes a light source array 40 comprising a plurality of LEDs 40a (seen in phantom view) that are electrically coupled to lead 11 via leads 40c. As discussed above, light source array 40 is preferably encapsulated in a light-transmissive polymer 23, or at least, in an epoxy that transmits the wavelengths of light required to activate the photoreactive agent introduced into the target tissue. Positioned immediately behind LEDs 40a (i.e., proximal of LEDs 40a) is a highly-reflective disk 40b. Any light emitted from LEDs 40a in a direction toward proximal end 8 is reflected back by reflective disk 40b towards distal end 6. Additionally, a reflective coating 43 (such as aluminum or another reflective material), is applied to the outer surface of body 4 adjacent to light source array 40. Any light from LEDs 40a directed to the sides (i.e., towards body 4) is redirected by reflective coating 43 towards distal end 6. Reflective disk 40b and reflective coating 43 thus cooperatively maximize the intensity of light delivered through distal end 6.

Light source array 40 is coupled to a focusing lens 42, which in turn, is coupled to an optical fiber bundle 44. Preferably, optical fiber bundle 44 tapers toward distal end 6, as shown in FIGS. 4A and 4B; however, it should be understood that this tapered shape is not required. Optical fiber bundle 44 is coupled to a light-diffusing tip 46. An expandable member 47 (such as an inflatable balloon) is included for centering light-generating apparatus 5 within a blood vessel and for occluding blood flow past distal end 6 that could reduce the amount of light delivered to the targeted tissue. The expandable member is preferably secured to distal end 6 so as to encompass light-diffusing tip 46. Expandable member 47 may be formed from a suitable biocompatible material, such as, polyurethane, polyethylene, fluorinated ethylene propylene (PEP), polytetrafluoroethylene (PIPE), or polyethylene terephthalate (PET).

It should be understood that while light source array 40 has been described as including a plurality of LEDs 40a disposed on conductive traces electrically connected to lead 11, light source array 40 can alternatively use other sources of light. As noted above, possible light sources include, but are not limited to, organic LEDs, super luminescent diodes, laser diodes, and light emitting polymers. While not shown in FIGS. 4A and 4B, it should be understood that light-generating apparatus 5 can beneficially incorporate a radio-opaque marker, as described above in conjunction with light-generating apparatus 1 (in regard to radio-opaque marker 17 in FIGS. 1A and 1B).

FIG. 5 schematically illustrates yet another embodiment of a light-generating catheter in accord with the present invention. This embodiment employs a linear light source array configured so that a more elongate treatment area can be illuminated. While the first and second embodiments described above use an elongate light diffusing element to illuminate an elongate treatment area, because the light diffusing elements are directing light, not generating light, increasing the length of the diffusing elements merely distributes the light over a greater area. If diffused over to great an area, insufficient illumination will be provided to each portion of the treatment site. The embodiment shown in FIG. 5 includes a linear light source array that enables an elongate treatment area to be illuminated with a greater amount of light than can be achieved using the embodiments shown in FIGS. 1-4B.

Referring to FIG. 5, light-generating apparatus 50 is illustrated. As with the embodiments described above (i.e., the light-generating apparatus shown in FIGS. 1 and 4), light-generating apparatus 50 is preferably based on a multi-lumen catheter and includes an elongate, flexible body formed from a suitable biocompatible polymer or metal, which includes a distal portion 52 and a proximal portion 54. A plurality of light emitting devices 53 are disposed on a flexible, conductive substrate 55 encapsulated in a flexible cover 56 (formed of silicone or other flexible and light transmissive material). Light emitting devices 53 and conductive substrate 56 together comprise a light source array. Preferably, light emitting devices 53 are LEDs, although other light emitting devices, such as organic LEDs, super luminescent diodes, laser diodes, or light emitting polymers can be employed. Each light emitting device 53 preferably ranges from about 1 cm to about 10 cm in length, with a diameter that ranges from about 0.5 mm to about 5 mm. Flexible cover 56 can be optically transparent or can include embedded light scattering elements (such as titanium dioxide particles) to improve the uniformity of the light emitted from light-generating apparatus 50. While not specifically shown, it should be understood that proximal portion 54 includes an electrical lead enabling conductive substrate 56 to be coupled to an external power supply and control unit, as described above for the embodiments that have already been discussed.

The array formed of light emitting devices 53 and conductive substrate 56 is disposed between proximal portion 54 and distal portion 52, with each end of the array being identifiable by radio-opaque markers 58 (one radio-opaque marker 58 being included on distal portion 52, and one radio-opaque marker 58 being included on proximal portion 54). Radio-opaque markers 58 comprise metallic rings of gold or platinum. Light-generating apparatus 50 includes an expandable member 57 (such as a balloon) preferably configured to encompass the portion of light-generating apparatus 50 disposed between radio-opaque markers 58 (i.e., substantially the entire array of light emitting devices 53 and conductive substrate 56). As discussed above, expandable member 57 enables occlusion of blood flow past distal portion 52 and centers the light-generating apparatus. Where expandable member is implemented as a fluid filled balloon, the fluid acts as a heat sink to reduce a temperature build-up caused by light emitting devices 53. This cooling effect can be enhanced if light-generating apparatus 50 is configured to circulate the fluid through the balloon, so that heated fluid is continually (or periodically) replaced with cooler fluid. Preferably, expandable member 57 ranges in size (when expanded) from about 2 mm to 10 mm in diameter. Preferably such expandable members are less than 2 mm in diameter when collapsed, to enable the apparatus to be used in a coronary vessel. Those of ordinary skill will recognize that catheters including an inflation lumen in fluid communication with an inflatable balloon, to enable the balloon to the inflated after the catheter has been inserted into a body cavity or blood vessel are well known. While not separately shown, it will therefore be understood that light-generating apparatus 50 (particularly proximal portion 54) includes an inflation lumen. When light emitting devices 53 are energized to provide illumination, expandable member 57 can be inflated using a radio-opaque fluid, such as Renocal 76™ or normal saline, which assists in visualizing the light-generating portion of light-generating apparatus 50 during computerized tomography (CT) or angiography. The fluid employed for inflating expandable member 57 can be beneficially mixed with light scattering material, such as Intralipid, a commercially available fat emulsion, to further improve dispersion and light uniformity.

Light-generating apparatus 50 is distinguished from light-generating apparatus 1 and 4 described above in that light-generating apparatus 1 and 4 are each configured to be positioned within a vessel or other passage using a guide wire that extends within lumen 18 substantially throughout the apparatus. In contrast, light-generating apparatus 50 is positioned at a treatment site using a guidewire 51 that does not pass through the portion of light-generating apparatus 50 that includes the light emitting devices. Instead, guidewire 51 is disposed external to light-generating apparatus 50—at least between proximal portion 54 and distal portion 52. Thus, the part of guidewire 51 that is proximate light emitting devices 53 is not encompassed by expandable member 57. Distal portion 52 includes an orifice 59*a*, and an orifice 59*b*. Guidewire 51 enters orifice 59*a*, and exits distal portion 52 through orifice 59*b*. It should be understood that guidewire 51 can be disposed externally to proximal portion 54, or alternatively, the proximal portion can include an opening at its proximal end through which the guidewire can enter the proximal portion, and an opening disposed proximal to light emitting devices 53, where the guidewire then exits the proximal portion.

The length of the linear light source array (i.e., light emitting devices 53 and conductive substrate 56) is only limited by the effective length of expandable member 57. If the linear array is made longer than the expandable member, light emitted from that portion of the linear array will be blocked by blood within the vessel and likely not reach the targeted tissue. As described below in connection with FIGS. 13A-14B, the use of a plurality of expandable members enables even longer linear light source arrays (i.e., longer than any single expandable member) to be used in this invention.

FIG. 6 schematically illustrates a light-generating apparatus 50*a* being positioned in an artery 61, to provide PDT to post PCTA lesions 60. Light-generating apparatus 50*a* is substantially similar to light-generating apparatus 50 described above, except for including additional light emitting devices 53*a* disposed in an opposed relationship with respect to light emitting devices 53, to enable light output from light-generating apparatus 50*a* in additional directions. Light-generating apparatus 50*a* thus enables lesions on opposing sides of artery 61 to be treated. In FIG. 6, light-generating apparatus 50*a* has been properly positioned relative to lesions 60 using radio-opaque markers 58, so as to treat the lesions with PDT (i.e., the lesions are generally disposed between the radio-opaque markers). In FIG. 7, expandable member 57 has been inflated to contact the walls of artery 61, thereby centering light-generating apparatus 50*a* within artery 61, and occluding blood flow through the artery, to ensure that light emitted from light emitting devices 53 and 53*a* reaches lesions 64 and is not blocked by blood in the artery. Guidewire 51 is removed, and the light emitting devices are energized to direct light of the required wavelengths to lesions 60, which have previously been treated with a photoreactive agent for diagnostic or therapeutic purposes.

FIGS. 8, 9A, and 9B are enlarged views of light source arrays that can be used in a light-generating apparatus in accord with the present invention. Light source array 80, shown in FIG. 8, includes a plurality of LEDs 86*a* and 86*b* that are coupled to a flexible, conductive substrate 82. LEDs 86*a* emit light of a first color, having a first wavelength, while LEDs 86*b* emit light of a different color, having a second wavelength. Such a configuration is useful if two different photoreactive agents have been administered, where each different photoreactive agent is activated by light of a different wavelength. Light source array 80 also includes one or more light sensing elements 84, such as photodiodes or a reference LED, similarly coupled to flexible, conductive substrate 82. Each light sensing element 84 may be coated with a wavelength-specific coating to provide a specific spectral sensitivity, and different light sensing elements can have different wavelength-specific coatings. While light source array 80 is configured linearly, with LEDs on only one side (as the array in light-generating apparatus 50*a* of FIG. 5), it will be understood that different color LEDs and light sensing elements can be beneficially included in any of the light source arrays described herein.

Because the light source arrays of the present invention are intended to be used in flexible catheters inserted into blood vessels or other body passages, it is important that the light source arrays be relatively flexible, particularly where a light source array extends axially along some portion of the catheter's length. Clearly, the longer the light source array, the more flexible it must be. Light source arrays 10 and 40 (FIGS. 1A/1B, and 4A/4B, respectively) are configured in a radial orientation, and light emitted form the light sources in those arrays is directed to the distal end of the respective catheters (light-generating apparatus 1 and 4). Because light source arrays 10 and 40 do not extend axially along a substantial portion of their respective catheters, the relatively flexibility of light source arrays 10 and 40 is less important. However, light source array 80 (FIG. 8), and the light source arrays of light-generating apparatus 50 and 50*a* (FIGS. 5 and 6, respectively), are linearly configured arrays that extend axially along a more significant portion of their respective catheters. A required characteristic of a catheter for insertion into a blood vessel is that the catheter be sufficiently flexible to be inserted into a vessel and advanced along an often tortuous path. Thus, light source arrays that extend axially along a portion of a catheter can unduly inhibit the flexibility of that catheter. FIGS. 9A and 9B schematically illustrate axially extending light source arrays that include strain relief features that enable a more flexible linear array to be achieved.

FIG. 9A shows a linear array 88*a* having a plurality of light emitting sources 90 (preferably LEDS, although other types of light sources can be employed, as discussed above) mounted to both a first flexible conductive substrate 92*a*, and a second flexible conductive substrate 92*b*. Flexible conductive substrate 92*b* includes a plurality of strain relief features 93. Strain relief features 93 are folds in the flexible conductive substrate that enable a higher degree of flexibility to be achieved. Note that first flexible conductive substrate 92*a* is not specifically required and can be omitted. Further, strain relief features 93 can also be incorporated into first flexible conductive substrate 92*a*.

FIG. 9B shows a linear array 88*b* having a plurality of light emitting sources 90 mounted on a flexible conductive substrate 92*c*. Note that flexible conductive substrate 92*c* has a crenellated configuration. As shown, light emitting sources 90 are disposed in each "notch" of the crenellation. That is, light emitting sources 90 are coupled to both an upper face 93*a* of flexible conductive substrate 92*c*, and a lower face 93*b* of flexible conductive substrate 92*c*. Thus, when light emitting sources 90 are energized, light is emitted generally outwardly away from both upper surface 93*a* and lower surface 93*b*. If desired, light emitting sources 90 can be disposed on only upper surface 93*a* or only on lower surface 93*b* (i.e., light emitting sources can be disposed in every other "notch"), so that light is emitted generally outwardly away from only one of upper surface 93*a* and lower surface 93*b*. The crenellated configuration of flexible conductive substrate 92*c* enables a higher degree of flexibility to be achieved, because each crenellation acts as a strain relief feature.

External bond wires can increase the cross-sectional size of an LED array, and are prone to breakage when stressed. FIGS. 1A and 1B illustrate leads 10*b* that are exemplary of such external bond wires. FIG. 9C schematically illustrates a flip-chip mounting technique that can be used to eliminate the need for external bond wires on LEDs 94 that are mounted on upper and lower surfaces 93*c* and 93*d* (respectively) of flexible conductive substrate 92*d* to produce a light source array 97. Any required electrical connections 95 pass through flexible conductive substrate 92d, as opposed to extending beyond lateral sides of the flexible conductive substrate, which would tend to increase the cross-sectional area of the array. Light source array 97 is shown encapsulated in a polymer layer 23. A guidewire lumen 98a is disposed adjacent to light source array 97. An expandable balloon 99 encompasses the array and guidewire lumen. Note that either, but not both, polymer layer 23 and expandable balloon 99 can be eliminated (i.e., if the expandable balloon is used, it provides protection to the array, but if not, then the polymer layer protects the array).

FIG. 9D shows a linear array 96 including a plurality of light emitting sources (not separately shown) that spirals around a guidewire lumen 98b. Once again, balloon 99 encompasses the guidewire lumen and the array, although if no balloon is desired, a polymer layer can be used instead, as noted above. For each of the implementations described above, the array of light sources may comprise one or more LEDs, organic LEDs, super luminescent diodes, laser diodes, or light emitting polymers ranging from about 1 cm to about 10 cm in length and having a diameter of from about 1 mm to about 2 mm.

Turning now to FIG. 10, a light-generating apparatus 100 is shown as the apparatus is being positioned in a blood vessel 101, to administer PDT to treatment areas 108. Light-generating apparatus 100 is simpler in construction than light-generating apparatus 1, 4, 50, and 50a (each of which is based on a catheter), because light-generating apparatus 100 is based on a guidewire. Light-generating apparatus 100 includes a main body 102, a light source array 104, and a spring tip 106. Main body 102 is based on a conventional guidewire, preferably having a diameter ranging from about 0.10 inches to about 0.060 inches. However, main body 102 is distinguishable from a conventional guidewire because main body 102 includes electrical lead 105. Spring tip 106 is also based on a conventional guidewire spring tip. Light source array 104 includes a plurality of light emitting devices 107, each electrically coupled to lead 105 (alternatively, each light emitting device is coupled to a flexible conductive substrate, that is in turn electrically coupled to lead 105). While not separately shown, it should be understood that radio-opaque markers can be included at each end of light source array 104, thereby enabling the light source array to be properly positioned relative to treatment areas 108.

In FIG. 11, light-generating apparatus 100 has been inserted into a balloon catheter 112, and the combination of balloon catheter 112 and light-generating apparatus 100 is shown being positioned in blood vessel 101, also to administer PDT to treatment areas 108. Balloon 114 has been inflated to contact the walls of blood vessel 101, thereby centering the combination of balloon catheter 112 and light-generating apparatus 100 within blood vessel 101 and occluding blood flow that could allow blood to block light emitted from light emitting devices 107 from reaching treatment areas 108. As discussed above, the fluid used to inflate the balloon should readily transmit the wavelengths of light required to activate the photoreactive agent(s) used to treat treatment areas 108. As described above, additives can be added to the fluid to enhance light transmission and diffusion. The fluid will also act as a heat sink to absorb heat generated by light emitting devices 107, and the beneficial effect of the fluid as a coolant can be enhanced by regularly circulating the fluid through the balloon.

FIGS. 12A-12D provide details showing how light emitting devices can be integrated into guidewires. Referring to FIG. 12A, a solid guidewire 120 includes a conductive core 124 and a plurality of compartments 121 formed in the guidewire around the conductive core. Conductive core 124 is configured to be coupled to a source of electrical energy, so that electrical devices coupled to conductive core 124 can be selectively energized by current supplied by the source. Compartments 121 can be formed as divots, holes, or slots in guidewire 120, using any of a plurality of different processes, including but not limited to, machining, and laser cutting or drilling. Compartments 121 can be varied in size and shape. As illustrated, compartments 121 are arranged linearly, although such a linear configuration is not required. Preferably, each compartment 121 penetrates sufficiently deep into guidewire 120 to enable light emitting devices 122 to be placed into the compartments and be electrically coupled to the conductive core, as indicated in FIG. 12B. A conductive adhesive 123 can be beneficially employed to secure the light emitting devices into the compartments and provide the electrical connection to the conductive core. Of course, conductive adhesive 123 is not required, and any suitable electrical connections can alternatively be employed. Preferably, LEDs are employed for the light emitting devices, although as discussed above, other types of light sources can be used. If desired, only one compartment 121 can be included, although the inclusion of a plurality of compartments will enable a light source array capable of simultaneously illuminating a larger treatment area to be achieved.

Once light emitting devices 122 have been inserted into compartments 121 and electrically coupled to conductive core 124, a second electrical conductor 126, such as a flexible conductive substrate or a flexible conductive wire, is longitudinally positioned along the exterior of guidewire 120, and electrically coupled to each light emitting device 122 using suitable electrical connections 128, such as conductive adhesive 123 as (illustrated in FIG. 12B) or wire bonding (as illustrated in FIG. 12C). Guidewire 120 (and conductor 126) is then coated with an insulating layer 129, to encapsulate and insulate guidewire 120 (and conductor 126). The portion of insulating layer 129 covering light emitting devices 122 must transmit light of the wavelength(s) required to activate the photoreactive agent(s). Other portions of insulating layer 129 can block such light transmission, although it likely will be simpler to employ a homogenous insulating layer that transmits the light. Additives can be included in insulating layer 129 to enhance the distribution of light from the light emitting devise, generally as described above.

As already noted above, using a plurality of expandable members enables a linear light source array that is longer than any one expandable member to be employed to illuminate a treatment area that is also longer than any one expandable member. FIGS. 13A, 13B, 14A, and 14B illustrate apparatus including such a plurality of expandable members. FIGS. 13A and 13B show an apparatus employed in connection with an illuminated guidewire, while FIGS. 14A and 14B illustrate an apparatus that includes a linear light source array combined with the plurality of expandable members. In each embodiment shown in these FIGURES, a relatively long light source array (i.e., a light source array having a length greater than a length of any expandable member) is disposed between a most proximally positioned expandable member and a most distally positioned proximal member.

FIG. 13A schematically illustrates a light-generating apparatus 131 for treating relatively long lesions (i.e., lesions of about of 60 mm in length or longer) in a blood vessel 137. Light-generating apparatus 131 is based on a multi-lumen catheter 130 in combination with an illuminated guidewire 135 having integral light emitting devices. Multi-lumen catheter 130 is elongate and flexible, and includes a plurality of expandable members 133a-133d. While four such expandable members are shown, alternatively, more or fewer expandable members can be employed, with at least two expandable members being particularly preferred. As discussed above, such expandable members occlude blood flow and center the catheter in the vessel. Multi-lumen catheter 130 and expandable members 133a-133d preferably are formed from a suitable bio-compatible polymer, including but not limited to polyurethane, polyethylene, PEP, PTFE, or PET. Each expandable member 133a-133d preferably ranges from about 2 mm to about 10 mm in diameter and from about 1 mm to about 60 mm in length. When inflated, expandable members 133a-133d are pressurized from about 1 atmosphere to about 16 atmospheres. It should be understood that between expandable member 133a and expandable member 133d, multi-lumen catheter 130 is formed of a flexible material that readily transmits light of the wavelengths required to activate the photoreactive agent(s) with which light-generating apparatus 131 will be used. Bio-compatible polymers having the required optical characteristics can be beneficially employed. As discussed above, additives such as diffusion agents can be added to the polymer to enhance the transmission or diffusion of light. Of course, all of multi-lumen catheter 130 can be formed of the same material, rather than just the portions between expandable member 133a and expandable member 133d. Preferably, each expandable member 133a-133d is similarly constructed of a material that will transmit light having the required wavelength(s). Further, any fluid used to inflate the expandable members should similarly transmit light having the required wavelength(s).

Referring to the cross-sectional view of FIG. 13B (taken along lines section lines A-A of FIG. 13A), it will be apparent that multi-lumen catheter 130 includes an inflation lumen 132a in fluid communication with expandable member 133a, a second inflation lumen 132b in fluid communication with expandable members 133b-c, a flushing lumen 134, and a working lumen 136. If desired, each expandable member can be placed in fluid communication with an individual inflation lumen. Multi-lumen catheter 130 is configured such that flushing lumen 134 is in fluid communication with at least one port 138 (see FIG. 13A) formed through the wall of multi-lumen catheter 130. As illustrated, a single port 138 is disposed between expandable member 133a and expandable member 133b and functions as explained below.

Once multi-lumen catheter 130 is positioned within blood vessel 137 so that a target area is disposed between expandable member 133a and expandable member 133d, inflation lumen 132a is first used to inflate expandable member 133a. Then, the flushing fluid is introduced into blood vessel 137 through port 138. The flushing fluid displaces blood distal to expandable member 133a. After sufficient flushing fluid has displaced the blood flow, inflation lumen 132b is used to inflate expandable members 133b, 133c, thereby trapping the flushing fluid in portions 137a, 137b, and 137c of blood vessel 137. The flushing fluid readily transmits light of the wavelength(s) used in administering PDT, whereas if blood were disposed in portions 137a, 137b, and 137c of blood vessel 137, light transmission would be blocked. An alternative configuration would be to provide an inflation lumen for each expandable member, and a flushing port disposed between each expandable member. The expandable members can then be inflated, and each distal region can be flushed, in a sequential fashion.

A preferred flushing fluid is saline. Other flushing fluids can be used, so long as they are non toxic and readily transmit light of the required wavelength(s). As discussed above, additives can be included in flushing fluids to enhance light transmission and dispersion relative to the target tissue. Working lumen 136 is sized to accommodate light emitting guidewire 135, which can be fabricated as described above. Multi-lumen catheter 130 can be positioned using a conventional guidewire that does not include light emitting devices. Once multi-lumen catheter 130 is properly positioned and the expandable members are inflated, the conventional guidewire is removed and replaced with a light emitting device, such as an optical fiber coupled to an external source, or a linear array of light emitting devices, such as LEDs coupled to a flexible conductive substrate. While not specifically shown, it will be understood that radio-opaque markers such as those discussed above can be beneficially incorporated into light-generating apparatus 131 to enable expandable members 133a and 133d to be properly positioned relative to the target tissue.

Still another embodiment of the present invention is light-generating apparatus 141, which is shown in FIG. 14A disposed in a blood vessel 147. Light-generating apparatus 141 is similar to light-generating apparatus 131 describe above, and further includes openings for using an external guide wire, as described above in connection with FIG. 5. An additional difference between this embodiment and light-generating apparatus 131 is that where light emitting devices were not incorporated into multi-lumen catheter 130 of light-generating apparatus 131, a light emitting array 146 is incorporated into the catheter portion of light-generating apparatus 141. FIGS. 1, 2, and 5 show exemplary configurations for incorporating light emitting devices into a catheter.

Light-generating apparatus 141 is based on an elongate and flexible multi-lumen catheter 140 that includes light emitting array 146 and a plurality of expandable members 142a-142d. Light emitting array 146 preferably comprises a linear array of LEDs. As noted above, while four expandable members are shown, more or fewer expandable members can be employed, with at least two expandable members being particularly preferred. The materials and sizes of expandable members 142a-142d are preferably consistent with those described above in conjunction with multi-lumen catheter 130. The walls of multi-lumen catheter 140 proximate to light emitting array 146 are formed of a flexible material that does not substantially reduce the transmission of light of the wavelengths required to activate the photoreactive agent(s) with which light-generating apparatus 141 will be used. As indicated above, bio-compatible polymers having the required optical characteristics can be beneficially employed, and appropriate additives can be used. Preferably, each expandable member is constructed of a material and inflated using a fluid that readily transmit light of the required wavelength(s).

Referring to the cross-sectional view of FIG. 14B (taken along section line B-B of FIG. 14A), it can be seen that multi-lumen catheter 140 includes an inflation lumen 143a in fluid communication with expandable member 142a, a second inflation lumen 143b in fluid communication with expandable members 142b-c, a flushing lumen 144, and a working lumen 149. Again, if desired, each expandable member can be placed in fluid communication with an individual inflation lumen. Multi-lumen catheter 140 is configured so that flushing lumen 144 is in fluid communication with a port 148 (see FIG. 14A) formed in the wall of multi-lumen catheter 140, which enables a flushing fluid to be introduced into portions 147a-147c of blood vessel 147 (i.e., into those portions distal of expandable member 142a). Those portions are isolated using inflation lumen 143b to inflate expandable members 142b-142d. The flushing fluid is selected as described above. Working lumen 149 is sized to accommodate light emitting array 146. Electrical leads 146b within working lumen 149 are configured to couple to an external power supply, thereby enabling the light source array to be selectively energized with an electrical current. A distal end 139 of multi-lumen catheter 140 includes an opening 160a in the catheter side wall configured to enable guidewire 145 (disposed outside of multi-lumen catheter 140) to enter a lumen (not shown) in the distal end of the catheter that extends between opening 160a and an opening 160b, thereby enabling multi-lumen catheter 140 to be advanced over guidewire 145.

FIG. 15 shows an alternative embodiment of the light-generating apparatus illustrated in FIGS. 13A, 13B, 14A, and 14B. A light-generating apparatus 150 in FIG. 15 is based on a multi-lumen catheter having an elongate, flexible body 154 formed from a suitable bio-compatible polymer and expandable members 152a-152d. As indicated above, at least two expandable members are particularly preferred. The difference between light-generating apparatus 150 and light-generating apparatus 131 and 141, which were discussed above, is that the expandable members in light-generating apparatus 150 are fabricated as integral portions of body 154, while the expandable members of light-generating apparatus 131 and 141 are preferably implemented as separate elements attached to a separate catheter body.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for using photodynamic therapy to treat vascular tissue, comprising the steps of:
   (a) providing a vascular illumination apparatus comprising:
      (i) an elongate, flexible body having a proximal end, a distal end, and at least one lumen; and
      (ii) a forward facing light source element that is disposed adjacent to the distal end of the elongate, flexible body, the forward facing light source element, when energized, emitting light having a characteristic emission waveband;
   (b) administering a photoreactive agent to target vascular tissue in a patient, the photoreactive agent having a characteristic absorption waveband corresponding to the characteristic emission waveband of the light source element;
   (c) advancing the vascular illumination apparatus through the vascular system of the patient until the forward facing light source element is disposed adjacent to the vascular target tissue, wherein the vascular illumination apparatus is advanced over a guidewire to properly position the forward facing light source element relative to the vascular target tissue; and
   (d) energizing the forward facing light source element to administer light to the vascular target tissue, the application of light to the vascular target tissue resulting in at least one of a therapeutic effect and generation of diagnostic data, such that when energized, light from the forward facing light source element is directed through an elongate linear light guide toward a diffusing distal tip of the vascular illumination apparatus, where the light is diffused before being directed to the vascular target tissue, the elongate linear light guide being disposed between the forward facing light source element and the diffusing distal tip.

2. The method of claim 1, wherein before the step of energizing the forward facing light source element, further comprising the step of centering the vascular illumination apparatus within a blood vessel that includes the vascular target tissue.

3. The method of claim 1, wherein before the step of energizing the forward facing light source element, further comprising the step of displacing a bodily fluid disposed between the forward facing light source element and the vascular target tissue, thereby preventing the bodily fluid from interfering with the transmission of light from the forward facing light source element to the target tissue.

4. The method of claim 3, wherein the step of displacing the bodily fluid disposed between the forward facing light source element and the target tissue before the step of energizing the forward facing light source element comprises the step of inflating an expandable member that substantially encompasses the forward facing light source element until the expandable member contacts the walls of the vascular lumen adjacent to the target tissue, thereby displacing bodily fluid that could interfere with the transmission of light from the forward facing light source element to the target tissue.

5. The method of claim 3, wherein the step of displacing the bodily fluid disposed between the forward facing light source element and the target tissue before the step of energizing the forward facing light source element comprises the steps of:
   (a) inflating a first expandable member disposed distal of the forward facing light source element and a second expandable member disposed proximal of the forward facing light source element until the first and the second expandable members contact the walls of the vascular lumen adjacent to the target tissue; and
   (b) replacing the bodily fluid trapped between the first expandable member and the second expandable member with a flush fluid.

6. The method of claim 1, wherein the step of energizing the forward facing light source element to administer light to the vascular target tissue, such that light is directed through the linear light guide, further comprises the step of directing the light through an optical fiber comprising the linear light guide.

7. The method of claim 6, wherein the step of directing the light through the optical fiber comprises the step of directing the light through an optical fiber that tapers from the forward facing light source element towards the diffusing tip disposed at the distal end of the vascular illumination apparatus.

8. A method for using photodynamic therapy to treat vascular tissue, comprising the steps of:
   (a) providing a vascular illumination apparatus comprising:
      (i) an elongate, flexible body having a proximal end and a distal end;
      (ii) at least one forward facing light source disposed adjacent to the distal end of the elongate, flexible body, the at least one forward facing light source, when energized, emitting light having a characteristic emission waveband;
      (iii) a diffusing distal tip; and
      (iv) a linear light guide disposed between the at least one forward facing light source and the diffusing distal tip;
   (b) administering a photoreactive agent to target vascular tissue in a patient, the photoreactive agent having a characteristic absorption waveband corresponding to the characteristic emission waveband of the at least one light source;

(c) advancing the vascular illumination apparatus through the vascular system of the patient until the at least one light source is disposed adjacent to the vascular target tissue;

(d) energizing the at least one light source to cause the at least one light source to emit light;

(e) directing the light emitted by the at least one light source toward a distal end of the vascular illumination apparatus along a linear path; and (f) diffusing and emitting light from the distal end of the vascular illumination apparatus to administer the light to the vascular target tissue, the application of the light to the vascular target tissue resulting in at least one of a therapeutic effect and generation of diagnostic data.

9. The method of claim 8, wherein the step of directing the light along the linear path comprises the step of directing the light through an optical fiber disposed between the at least one light source and a diffusing tip disposed at the distal end of the vascular illumination apparatus.

10. The method of claim 9, wherein the step of directing the light through the optical fiber comprises the step of directing the light through an optical fiber that tapers from the at least one light source towards the diffusing tip disposed at the distal end of the vascular illumination apparatus.

11. A method for using photodynamic therapy to treat vascular tissue, comprising the steps of:

(a) providing a vascular illumination apparatus comprising an elongate flexible body having a proximal end, a distal end, a guidewire that includes a light emitting portion proximate the distal end, the light emitting portion including at least one light source, and at least one expandable member overlapping the light emitting portion;

(b) administering a photoreactive agent to target vascular tissue in a patient, the photoreactive agent having a characteristic absorption waveband corresponding to the characteristic emission waveband of the light source element (c) advancing the vascular illumination apparatus through the vascular system of the patient until the light emitting portion is disposed adjacent to the vascular target tissue, such that a guidewire is slidably disposed in the elongate flexible body;

(d) actuating the at least one expandable member to fix a position of the light emitting portion relative to the vascular target tissue;

(e) advancing a light emitting member through the elongate flexible body until the light emitting member is proximate the light emitting portion of the vascular illumination apparatus; and (f) activating the light emitting member portion of the guidewire to cause light to be emitted from the light emitting portion of the vascular illumination apparatus to administer light to the vascular target tissue, the application of light to the vascular target tissue resulting in at least one of a therapeutic effect, and generation of diagnostic data.

12. The method of claim 11, wherein the step of activating the light emitting member comprises the step of energizing the at least one light source.

13. The method of claim 11, wherein the step of actuating the at least one expandable member comprises the step of actuating a plurality of expandable members, the plurality of expandable members extending generally from a proximal end of the light emitting portion to a distal end of the light emitting portion.

14. The method of claim 12, wherein the step of actuating the plurality of expandable members comprises the step of actuating the plurality of expandable members individually.

15. The method of claim 12, wherein the step of actuating the plurality of expandable members comprises the step of actuating the plurality of expandable members sequentially.

16. The method of claim 12, wherein the step of actuating the plurality of expandable members comprises the step of actuating the plurality of expandable members simultaneously.

* * * * *